(12) United States Patent
Juo et al.

(10) Patent No.: US 8,673,875 B2
(45) Date of Patent: Mar. 18, 2014

(54) METHOD FOR TREATING ATHEROSCLEROSIS

(71) Applicant: Kaohsiung Medical University, Kaohsiung (TW)

(72) Inventors: Suh-Hang Hank Juo, Kaohsiung (TW); Yung-Song Wang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 13/710,478

(22) Filed: Dec. 11, 2012

(65) Prior Publication Data

US 2013/0089601 A1 Apr. 11, 2013

Related U.S. Application Data

(63) Continuation-in-part of application No. 12/635,178, filed on Dec. 10, 2009, now Pat. No. 8,354,520.

(51) Int. Cl.
*A61K 48/00* (2006.01)

(52) U.S. Cl.
USPC ......... 514/44; 536/24.5; 536/24.31; 536/24.1

(58) Field of Classification Search
None
See application file for complete search history.

(56) References Cited

U.S. PATENT DOCUMENTS

2006/0105360 A1   5/2006   Croce et al.

OTHER PUBLICATIONS

Costinean et al., "Pre-B cell proliferation and lymphoblastic leukemia/high-grade lymphoma in Eµ-miR155 transgenic mice", PNAS, vol. 103, No. 18, 7024-7029, May 2, 2006, The National Academy of Sciences of the USA.
Ambros, "The functions of animal microRNAs", Nature, vol. 431, 350-355, Sep. 16, 2004, Nature Publishing Group.
Hwang et al., "MicroRNAs in cell proliferation, cell death, and tumorigenesis", British Journal of Cancer, 94, 776-780, Feb. 21, 2006, Cancer Research UK.
Esquela-Kerscher et al., "Oncomirs—microRNAs with a role in cancer", Nature Reviews | Cancer, vol. 6, 259-269, Apr. 2006, Nature Publishing Group.
Lagos-Quintana et al., "Identification of Tissue-Specific MicroRNAs from Mouse", Current Biology, vol. 12, 735-739, Apr. 30, 2002, Elsevier Science Ltd.
Van Rooij et al., "A signature pattern of stress-responsive microRNAs that can evoke cardiac hypertrophy and heart failure", PNAS, vol. 103, No. 48, 18255-18260, Nov. 28, 2006, The National Academy of Sciences of the USA.
Ji et al., "MicroRNA Expression Signature and Antisense-Mediated Depletion Reveal an Essential Role of MicroRNA in Vascular Neointimal Lesion Formation", Circ. Res., 100, 1579-1588, 2007.
Song et al., "Simvastatin reduces atherogenesis and promotes the expression of hepatic genes associated with reverse cholesterol transport in apoE-knockout mice fed high-fat diet", Lipids in Health and Disease 2011, 10:8.

*Primary Examiner* — Kimberly Chong
(74) *Attorney, Agent, or Firm* — Pai Patent & Trademark Law Firm; Chao-Chang David Pai

(57) ABSTRACT

The invention provides a method for treating atherosclerosis in a subject in need thereof, including administering an effective amount of microRNA-195 to the subject in need thereof. The microRNA-195 may be packaged in a pharmaceutically acceptable carrier. Moreover, the pharmaceutically acceptable carrier may includes a liposome, lipid particle or viral vector.

12 Claims, 14 Drawing Sheets

METHOD FOR TREATING ATHEROSCLEROSIS

CROSS REFERENCE TO RELATED APPLICATIONS

This application is a Continuation-In-Part of pending U.S. patent application Ser. No. 12/635,178, filed Dec. 10, 2009 and entitled "Composition and method for treating atherosclerosis, method for determining if a subject has atherosclerosis and method of screening of an anti-atherosclerosis drug" which is disclosed herein in the entirety.

INCORPORATION BY REFERENCE OF SEQUENCE LISTING

A sequence listing submitted as a text file via EFS-Web is incorporated herein by reference. The text file containing the sequence listing is named "0911-A51775-CIP-US_Seq_Listing.txt"; its date of creation was Nov. 14, 2012; and its size is 1,566 bytes.

BACKGROUND OF THE INVENTION

1. Field of the Invention

The present invention relates to applications of microRNA-195, and in particular relates to applications of microRNA-195 with regard to atherosclerosis treatment and detection.

2. Description of the Related Art

MicroRNAs (miRNAs) are single-stranded RNA molecules of about 21-23 nucleotides in length, which regulate gene expression. MiRNAs are first transcribed as a pri-miRNA with a cap and a poly-A tail and then processed to short, 70-nucleotide stem-loop structures known as pre-miRNA in a cell nucleus. The pre-miRNAs are then processed to mature miRNAs in the cytoplasm. A mature miRNA is complementary to a part of one or more messenger RNAs (mRNAs). Animal miRNAs are usually complementary to a site in the 3' untranslated region (UTR). Annealing of the miRNA to the mRNA inhibits protein translation, but sometimes facilitates cleavage of the mRNA.

MiRNAs are important regulators for cell growth, differentiation, and apoptosis (Costinean S, et al. Proc Natl Acad Sci USA. 2006; 103:7024-7029, Ambros V. 2004; 431:350-355 and Hwang H W, et al. Br J Cancer 2006; 94:776-780). Therefore, miRNAs may be important for normal development and physiology of cells. Consequently, dysregulation of miRNA may lead to human diseases. In this respect, an exciting research area is the role of miRNAs in cancer, given that cell dedifferentiation, growth, and apoptosis are important cellular events during the development of cancer. MiRNAs are currently thought to function as both tumor suppressors and oncogenes (Esquelq-Kerscher A, et al. Nature Reviews Cancer. 2006; 6:259-269). Although miRNAs are expressed in the cardiovascular system (Lagos-Quintana M, et al. Curr Biol. 2002; 12:735-739), the role of miRNAs in atherosclerotic diseases are almost completely unknown. However, few studies have revealed the importance of miRNAs in cardiomyopathies (van Rooij E, et al. Proc Natl Acad Sci U S A. 2006; 103:18255-18260). Nevertheless, the role of miRNAs in atherosclerotic diseases has yet to be fully investigated.

A tissue-specific expression is one important characteristic of miRNA expression. Specifically, one miRNA may be highly expressed in one tissue but have no or low expression in other tissues (Lagos-Quintana M, et al. Curr Biol. 2002; 12:735-739). A recent study using a rat model showed that 140 out of 180 tested miRNAs were expressed in the rat carotid arteries and 49 of the 140 were highly expressed in the rat normal arteries (Ji R, et al. Circ Res. 2007; 100:1579-1588).

BRIEF SUMMARY OF THE INVENTION

The invention provides a composition for treating atherosclerosis, comprising: an effective amount of microRNA-195 as an active ingredient for treating atherosclerosis; and a pharmaceutically acceptable carrier or salt.

The invention also provides a method for treating atherosclerosis in a subject in need thereof, comprising, administering an effective amount of microRNA-195 to the subject in need thereof.

The invention further provides a method for determining if a subject has atherosclerosis, comprising: determining an endogenous microRNA-195 expression level of a subject suspected of having atherosclerosis; and comparing the endogenous microRNA-195 expression level of the subject with an endogenous microRNA-195 expression level of a normal group, wherein an increase in the endogenous microRNA-195 expression level of the subject as compared to the endogenous microRNA-195 expression level of the normal group indicates that the subject has atherosclerosis.

The invention further provides a method of screening an anti-atherosclerotic drug, comprising: treating a subject with an atherosclerosis inducing compound and a candidate drug; determining an endogenous microRNA-195 expression level of the subject; and comparing the endogenous microRNA-195 expression level of the subject with an endogenous microRNA-195 expression level of a control only treated with the atherosclerosis inducing compound, wherein a decrease in the endogenous microRNA-195 expression level of the subject as compared to the endogenous microRNA-195 expression level of the control indicates that the candidate drug has potential for treating atherosclerosis.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
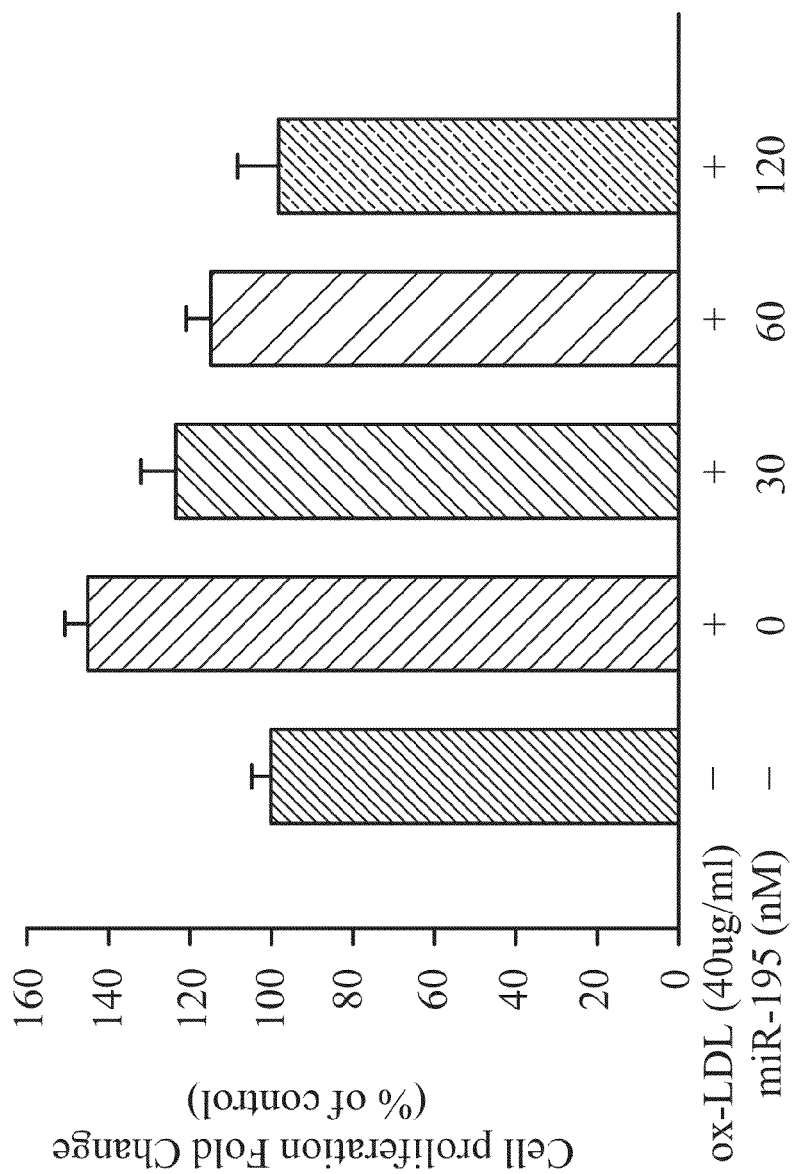
FIG. 1 shows the WST-1 assay results for cell proliferation of the vascular smooth muscle cells (VSMC) treated with different concentrations of microRNA-195 (miR-195)

The following description is of the best-contemplated mode of carrying out the invention. This description is made for the purpose of illustrating the general principles of the invention and should not be taken in a limiting sense. The scope of the invention is best determined by reference to the appended claims.

The invention is based on a discovery that microRNA-195 (miR-195) is related to atherosclerosis and is able to be used for treating atherosclerosis.

The "microRNA-195" in the invention refers to an original microRNA-195, a modified microRNA-195 (for example, a pre-microRNA-195 or all pyrimidine nucleotides in microRNA are replaced by their 2'-O-methyl analogs to improve microRAN stability) or a mimic of a microRNA-195 (for example, a synthetic microRNA-195 duplex). In one embodiment, the microRNA-195 may comprise an original human microRNA-195 (the sequence of which is SEQ ID NO: 1), a modified human microRNA-195, for example, a human pre-microRNA-195 (the sequence of which is SEQ ID NO: 2 and consists of the sequence of original human microRNA-195, as set forth in SEQ ID NO: 1, starting from the 15$^{th}$ nucleotide) or a mimic of a human microRNA-195, for example, a synthetic microRNA-195 (such as Pre-miR miRNA, hsa-miR-195 (product ID PM10827), Ambion Inc.).

The invention uses a composition comprising a microRNA-195 as an active ingredient for treating atherosclerosis. The invention further provides a use for microRNA-195 for preparing a medicament for treating atherosclerosis. In one embodiment, the composition may comprise an effective amount of microRNA-195 and a pharmaceutically acceptable carrier or salt. In one embodiment, the microRNA-195 may be optionally packaged in the pharmaceutically acceptable carrier.

In another embodiment, a statin may be used in the composition of the invention. The statin may include, but is not limited to, simvastatin. Simvastatin is a lipid lowering drug belonging to the class of pharmaceuticals called "statins or HMGCoA reductase inhibitor." The composition of the invention may further comprise an effective amount statin. It is used to treat hypercholesterolemia (elevated cholesterol levels) and to prevent atherosclerotic diseases, such as myocardial infarction or stroke. The anti-atherosclerosis effect of the composition containing microRNA-195 along with statin is better than that of the composition containing only microRNA-195 and that of statin. The microRNA-195 and statin have a synergistic effect for treating atherosclerosis.

Panax Notoginseng is a widely used Chinese herb for the treatment of cardiovascular diseases, especially atherosclerosis. In another embodiment, a water extract of Panax Notoginseng or saponin which is the active ingredient of Panax Notoginseng may be used in the composition of the invention. The composition of the invention may further comprise an effective amount of water extract of Panax Notoginseng or saponin. The anti-atherosclerosis effect of the composition containing microRNA-195 along with the water extract of Panax Notoginseng or saponin is better than that of the composition containing only microRNA-195.

A method for treating atherosclerosis may be also included in the invention. The method for treating atherosclerosis may comprise administering an effective amount of a microRNA-195 to a subject in need thereof. The subject may comprise a mammal and in one embodiment, the mammal may comprise a human. In one embodiment, the microRNA-195 may be optionally packaged in a pharmaceutically acceptable carrier.

In another embodiment, the method for treating atherosclerosis may further comprise administering an effective amount of statin to a subject. The statin may include, but is not limited to, simvastatin. It is noted that the microRNA-195 and the statin may be administered at the same time or microRNA-195 may be administered first or statin may be administered first. The anti-atherosclerosis effect for administering microRNA-195 along with statin is better than that of administering only microRNA-195 and that of administering only statin. The microRNA-195 and statin have a synergistic effect for treating atherosclerosis. Furthermore, microRNA-195 may enhance statin effect for treating atherosclerosis and reduce the statin dose or reduce the statin-induced side effects for treating atherosclerosis.

In another embodiment, the method for treating atherosclerosis may further comprise administering an effective amount of water extract of Panax Notoginseng or saponin which is the active ingredient of Panax Notoginseng to a subject. It is noted that the microRNA-195 and the water extract of Panax Notoginseng or saponin may be administered at the same time or microRNA-195 may be administered first or the water extract of Panax Notoginseng or saponin may be administered first. The anti-atherosclerosis effect for administering microRNA-195 along with the water extract of Panax Notoginseng or saponin is better than that of administering only microRNA-195.

A pharmaceutically acceptable carrier may comprise, but is not limited to, a solvent, a dispersion medium, a liposome, a lipidic particle, a coating, a viral vector, a plasmid vector, or an isotonic and absorption delaying agent. The viral vector may include, but is not limited to, an adenovirus, an adeno-associated virus, a vaccinia virus, a retrovirus (lentivirus), etc. The pharmaceutical composition can be formulated into dosage forms for different administration routes utilizing conventional methods.

The pharmaceutically acceptable salt may comprise, but is not limited to, inorganic cation salts including alkali metal salts such as sodium salt, potassium salt or amine salt, alkaline-earth metal salt such as magnesium salt or calcium salt, the salt containing bivalent or quadrivalent cation such as zinc salt, aluminum salt or zirconium salt. In addition, the pharmaceutically acceptable salt may also comprise organic salt including dicyclohexylamine salt, methyl-D-glucamine, and amino acid salt such as arginine, lysine, histidine, or glutamine.

The composition of the invention may be administered orally, para-enterally or by an inhalation spray or via an implanted reservoir. Also the administration route in the method for treating atherosclerosis may comprise oral administration or para-enteral administration.

An oral composition can comprise, but is not limited to, tablets, capsules, emulsions and aqueous suspensions, dispersions and solutions.

Orally administered preparations may be in the form of solids, liquids, emulsions, suspensions, or gels, or preferably in a unit dosage form, for example as tablets or capsules. Tablets may be compounded in combination with other ingredients customarily used, such as talc, vegetable oils, polyols, gums, gelatin, starch, and other carriers. The lipid vesicles may be dispersed in or combined with a suitable liquid carrier in solutions, suspensions, or emulsions.

Para-enteral compositions intended for injection, either subcutaneously, intramuscularly, or intravenously, can be prepared with liquids or solid forms for a solution in liquid prior to injection, or as emulsions. Such preparations are sterile, and liquids to be injected intravenously should be isotonic. Suitable excipients are, for example, water, dextrose, saline, and glycerol.

Para-enteral administration is generally characterized by injection. The para-enteral method may comprise subcutaneous, intracutaneous, intravenous, intramuscular, intraarticular, intraarterial, intrasynovial, intrasternal, intrathecal, and intraleaional, as well as infusion techniques. A more recently revised approach for para-enteral administration involves use of a slow release or sustained release system, such that a constant level of dosage is maintained.

In the present invention, it was discovered that the endogenous microRNA-195 expression level of subjects with atherosclerosis were higher than that of healthy subjects, and that may due to a nature defense mechanism. The endogenous microRNA-195 may be used as a biomarker for atherosclerosis. A method for determining if a subject has atherosclerosis is provided in the invention. The method for determining if a subject has atherosclerosis may comprise the steps as described in the following.

First, an endogenous microRNA-195 expression level of a subject suspected of having atherosclerosis may be determined. The subject may comprise a mammal and the mammal may comprise human. In one embodiment, the endogenous microRNA-195 expression level of the subject may be determined by analyzing a sample of the subject. The sample may comprise plasma, serum or a tissue, etc. In one embodiment, the tissue may comprise blood vessel walls.

Next, the endogenous microRNA-195 expression level of the subject and an endogenous microRNA-195 expression level of a normal group are compared. An increase in the endogenous microRNA-195 expression level of the subject as compared to the endogenous microRNA-195 expression level of the normal group may indicate that the subject may have atherosclerosis. In one embodiment, the endogenous microRNA-195 expression level of the normal group may be a mean of an endogenous microRNA-195 expression level of the respective normal group subjects.

In addition, in the present invention, it was further discovered that when an atherosclerosis inducing compound treated cell is treated with the anti-atherosclerosis medicine known in the art, such as statin or Panax Notoginseng, the endogenous microRNA-195 expression level of the cell was lower when compared with that of an atherosclerosis inducing compound treated cell which was not treated with the anti-atherosclerosis medicine. Therefore, the endogenous microRNA-195 may be used as a drug target for screening an anti-atherosclerotic drug. A method of screening an anti-atherosclerotic drug is provided in the invention. The method of screening an anti-atherosclerotic drug may comprise the steps as described in the following.

First, a subject is treated with an atherosclerosis inducing compound and a candidate drug. The atherosclerosis inducing compound and the candidate drug may be treated to the subject at the same time. The subject may comprise a cell or mammal. The cell may comprise a vascular smooth muscle cell. The atherosclerosis inducing compound may comprise ox-LDL.

Next, an endogenous microRNA-195 expression level of the subject may be determined. When the subject is a mammal, the endogenous microRNA-195 expression level of the subject may be determined by analyzing a sample of the subject and the sample may comprise plasma, serum or a tissue, etc. In one embodiment, the tissue may comprise blood vessel walls.

Then, the endogenous microRNA-195 expression level of the subject and an endogenous microRNA-195 expression level of a control only treated with the atherosclerosis inducing compound are compared. A decrease in the endogenous microRNA-195 expression level of the subject as compared to the endogenous microRNA-195 expression level of the control may indicate that the candidate drug has potential for treating atherosclerosis.

In the present invention, first, microRNA-195 can be used to treat or prevent atherosclerosis. Second, a combined therapy method comprising statin or Panax Notoginseng with microRNA-195 may be used to increase therapeutic effect of atherosclerosis. Third, microRNA-195 may be used as a biomarker for determining atherosclerosis. Fourth, microRNA-195 can be used as a biomarker to screen compounds/drugs to find potential anti-atherosclerosis drugs.

EXAMPLE

Part 1: Cell Culture

The experiments were conducted in the primary aortic smooth muscle cells (purchased as cryopreserved tertiary cultures from Cascade Biologics, OR, USA) at passages 4 to 8. The VSMC cells were maintained in an M231 culture medium supplemented with fetal bovine serum (FBS, 5%), human epidermal growth factor (10 ng/ml), human basic fibroblast growth factor (3 ng/ml), insulin (10 mg/ml), penicillin (100 units/ml), streptomycin (100 pg/ml), and Fungizone (1.25 mg/ml). The cultures were kept at a temperature of 37° C. in an atmosphere of 5% $CO_2$ in air.

Part 2: Global MicroRNA Detection

Control cells were treated with ox-LDL (concentration of 40 μg/ml) that was used as a stimulant for atherosclerosis, and experimental cells were treated with ox-LDL (concentration of 40 μg/ml) and the Chinese herbal medicine Panax Notoginseng (in a form of water extract with concentration of 1 mg/ml; Chuang Song Zong Pharmaceutical co. Ltd). After a 4 hour treatment, cytoplasmic RNA was extracted from the cultured cells using a Trizol reagent (Invitrogen) according to the manufacturer protocol. The concentration and integrity of total RNA were determined using the NanoPhotometer™ spectrophotometer (IMPLEN GmbH, Munich, Germany). The global microRNA expression profile was measured using the TaqMan Array Human MicroRNA Array Set V.2.0® (Applied Biosystems Inc. ABI). The endogenous abundance of microRNAs was analyzed in an ABI PRIZM 7900 sequence detection system. Differentially expressed miRNAs were calculated by StatMiner software. The results are shown in Table 1.

Table 1: MicroRNA expression profile of VSMC after a Chinese herbal medicine (Panax Notoginseng) treatment

|  | Up regulation | Fold change |  | Down regulation | Fold change |
|---|---|---|---|---|---|
| Top 10 | miR-204 | 2.18 | Top 10 | miR-195 | 5.12 |
|  | miR-106b | 1.81 |  | miR-379 | 4.34 |
|  | miR-223 | 1.76 |  | miR-20a | 2.35 |
|  | miR-485 | 1.64 |  | miR-15b | 2.34 |
|  | miR-433 | 1.46 |  | miR-137 | 2.29 |
|  | miR-425 | 1.41 |  | Let-7b | 2.21 |
|  | miR-532 | 1.39 |  | miR-92a | 2.17 |
|  | miR-495 | 1.23 |  | miR-431 | 1.99 |
|  | miR-191 | 1.14 |  | miR-221 | 1.96 |
|  | miR-214 | 1.10 |  | miR-30b | 1.94 |

As shown in Table 1, among the 667 microRNAs in the array, 7 microRNAs showed decreased expression by at least 2-fold in the cells treated with the Chinese herbal medicine Panax Notoginseng. Three of the seven microRNAs with decreased expressions were in the miR-15 family, and microRNA-195 showed the most significant decrease. Accordingly, microRNA-195 was identified as a potential anti-atherosclerotic biomarker.

Part 3: Confirming a Novel Anti-Atherosclerotic Effect of miRNA-195

According to the global microRNA expression data, it was shown that microRNA-195 had the most significant change between treated and untreated cells with Panax Notoginseng. Then, microRNA-195 (Pre-miR miRNA, hsa-miR-195 (product ID PM10827), Ambion Inc., which mimics precursor for mature human miR-195) was transfected into the VSMC cells simultaneously treated with ox-LDL to confirm the miRNA-195 anti-atherosclerosis effect.

The transfection was performed using a siPort NeoFx reagent (Ambion) and VSMC cell proliferation and migration were evaluated 24 hours after the microRNA-195 transfection. In addition, simvastatin was used, a widely used lipid lowering drug and anti-atherosclerosis drug, to test the influence of microRNA-195 levels by simvastatin.

Cell Proliferation Assay

VSMC is an established model for atherosclerosis studies and when atherosclerosis incursion VSMC proliferation increases. A VSMC proliferation rate was used as a surrogate for the development of atherosclerosis, which was assessed by WST-1. By using a 1-3 µL siPort NeoFx (Ambion) reagent, 0-120 nM of microRNA-195 (Pre-miR™ miRNA, hsa-miR-195 (product ID PM10827), Ambion Inc.) was transfected into the VSMC cells while they were incubated with ox-LDL (40 µg/ml) for 24 hours. To measure cell proliferation, the microplates were incubated at a temperature of 37° C. with 5% $CO_2$ in air for 24 hours, after which 10 µL of WST-1 (Roche Applied Science, Indianapolis, Ind.) was added into each well and incubated for 30 minutes at a temperature of 37° C. The microplates were then read by a spectrophotometer by measuring the absorbance of a dye with a wavelength of 450 nm and a reference wavelength of 600 nm (Benchmark PLUS Microplate Spectrophotometer, Bio-Rad) and plotted. Each experiment had three replications. The results are shown in FIG. 1.

As shown in FIG. 1, ox-LDL (40 µg/ml) caused a significant increase in the cell proliferation by 144.8% over the basal level using the WST-1 assay. Transfecting microRNA-195 with concentrations of 30, 60 and 120 nM resulted in a concentration-dependent reduction of VSMC cell proliferation by 21%, 29% and 45%, respectively. It is shown that microRNA-195 exerts a dose-dependent effect on anti-proliferation.

Figure 2:
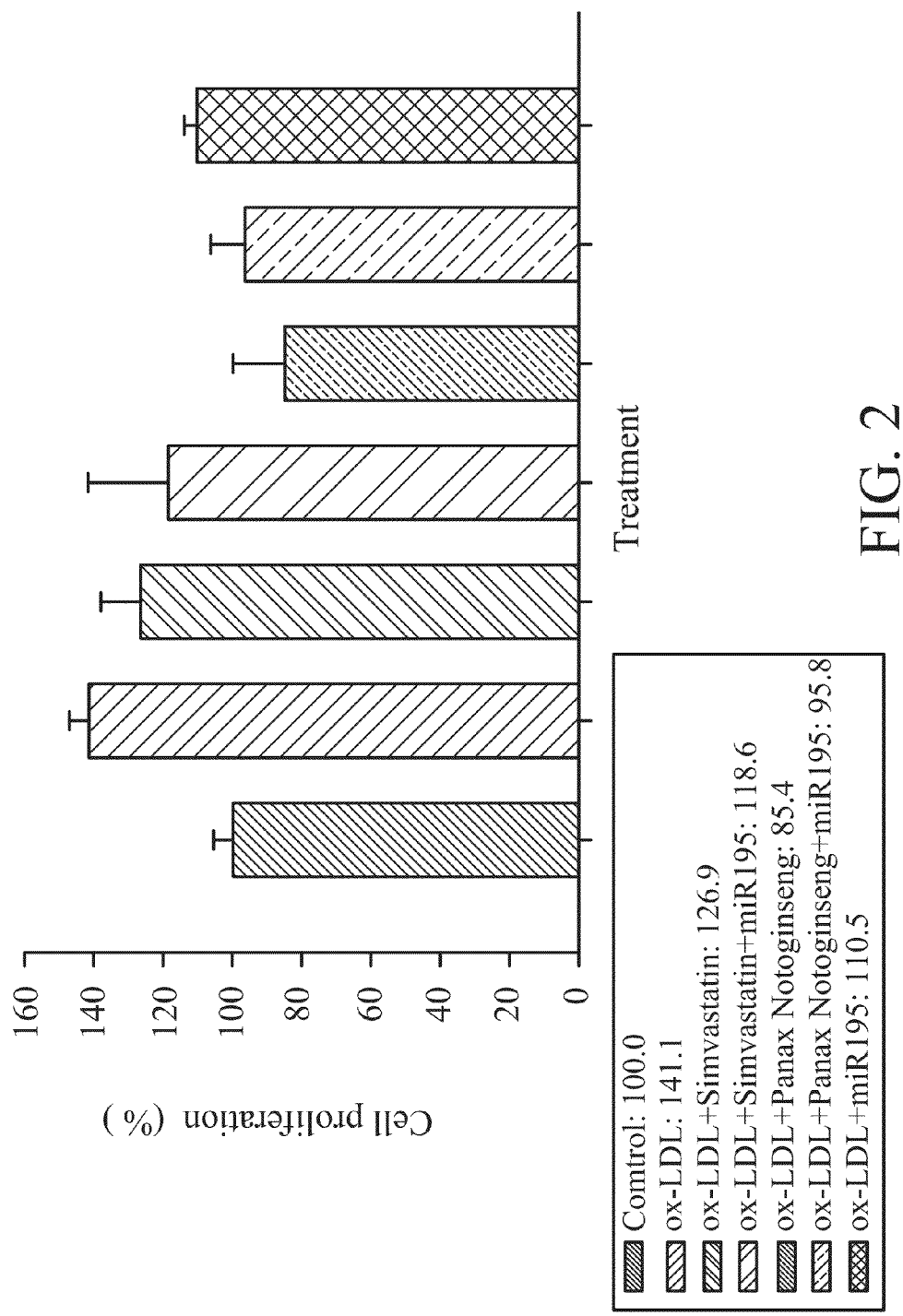
FIG. 2 shows the WST-1 assay results for cell proliferation of the VSMC cells with different treatments.

Cell proliferation of the VSMC was evaluated following incubation in ox-LDL (40 µg/ml) for 24 hours in the presence of microRNA-195 (Pre-miR miRNA, hsa-miR-195 (product ID PM10827), Ambion Inc.) (100 nM), simvastatin (1 nM) or Panax Notoginseng (in a form of water extract with concentration of 1 mg/ml; Chuang Song Zong Pharmaceutical co. Ltd), or in the presence of microRNA-195 (100 nM) with simvastatin (1 nM) or with Panax Notoginseng (in a form of water extract with concentration of 1 mg/ml). The WST-1 assay was also used to compare the cell proliferation level (anti-atherosclerotic effect) among the different treatments. The results are shown in FIG. 2. As shown in FIG. 2, the results indicated that the inhibition of the VSMC proliferation was stronger when the cells were treated with microRNA-195 plus simvastatin (1 nM) compared with microRNA-195 or simvastin alone. Our results suggest that microRNA-195 and simvastatin had a synergistic effect for treating atherosclerosis. Accordingly, microRNA-195 may enhance simvastatin effect for treating atherosclerosis and reduce the simvastatin dose or reduce the simvastatin-induced side effects for treating atherosclerosis.

Chemotactic Migration

Chemotactic migration is another characteristic of atherosclerosis and can be used as another line of evidence of atherosclerotic change for the cultured VSMC cells. This experiment was assayed by using a microchemotactic chamber and polycarbonate filters with pores of 8 mm in diameter (Transwell, Millipore). After incubated with microRNA-195 (Pre-miR miRNA, hsa-miR-195 (product ID PM10827), Ambion Inc.) (100 nM) or an inhibitor (100 nM) for 24 hours, the VSMC cells were trypsinized and suspended with a serum free medium. A volume (300 µl) of a $1 \times 10^4$ cell suspension was placed in the upper chamber, the medium containing ox-LDL (40 µg/ml, each) was placed in the lower and upper chamber. The cell suspension was incubated at a temperature of 37° C. under 5% $CO_2$ in air for 24 hours. After incubation, the VSMC cells on the upper side of the filter were scraped off, and the cells that had directly migrated to the lower side of the filter were trypsinized. The cells were fixed with methanol and stained with a Giemsa solution (Merck). Quantification of chemotactic migration was performed using the hemocytometer. The results were expressed as percentages of migrated cells as compared to the control medium cells and shown in FIG. 3.

Figure 3:
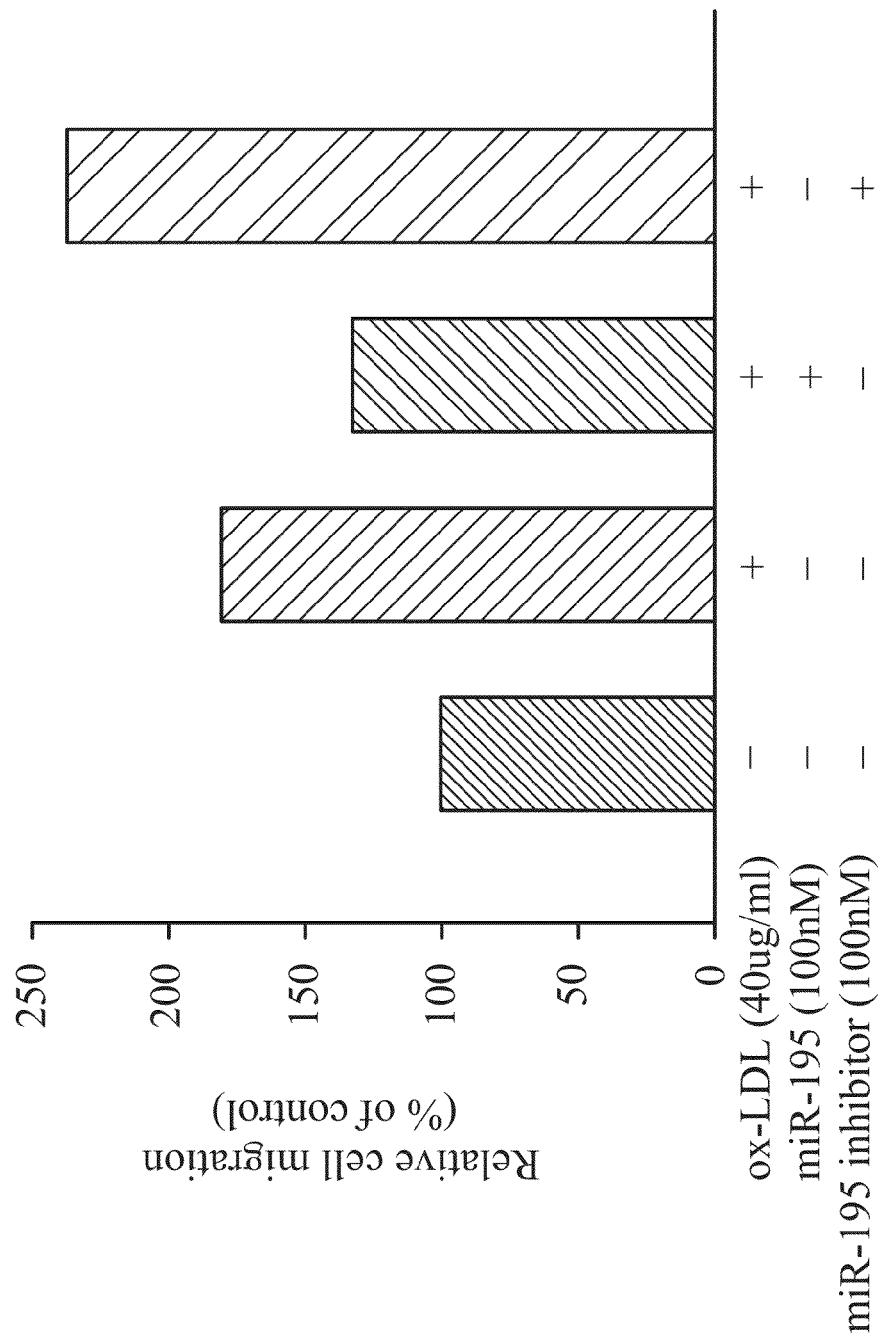
FIG. 3 shows the cell migration level of the VSMC cells treated with microRNA-195 and microRNA-195 inhibitor.

As shown in FIG. 3, ox-LDL (40 µg/ml) significantly stimulated chemotactic migration by 180.1% over the basal level. In the presence of microRNA-195 (Pre-miR miRNA, hsa-miR-195 (product ID PM10827), Ambion Inc.) (100 nM), the migration was significantly suppressed to 137.6%. Meanwhile, using the microRNA-195 inhibitor (100 nM) significantly increased migration to 233.7% in comparison to the control. Since VSMC migration is also a cellular phenotype to indicate atherosclerosis, the results shown in FIG. 3 clearly demonstrate that microRNA-195 has an anti-atherosclerosis effect.

The Influence of miRNA-195 on an Atherosclerotic Biomarker

Monocyte chemotactic protein-1 (MCP-1) is a well established atherosclerotic biomarker and it was examined to further test for the influence of microRNA-195 on the atherogenic biomarker. VSMC cells in six-well plates were grown to confluence and then cultivated in a serum-free medium for 24 hours before the experiment. After transfection of microRNA-195 for 24 hours, the cells were further incubated with ox-LDL and simvastatin for another 24 hours. The supernatants of the conditioned medium were collected and frozen at −70° C. The culture supernatants were analyzed to determine the MCP-1 using Sandwich Enzyme Immunoassay kits (BD Biosciences) according to the manufacturer protocol. The results are shown in FIG. 4.

Figure 4:
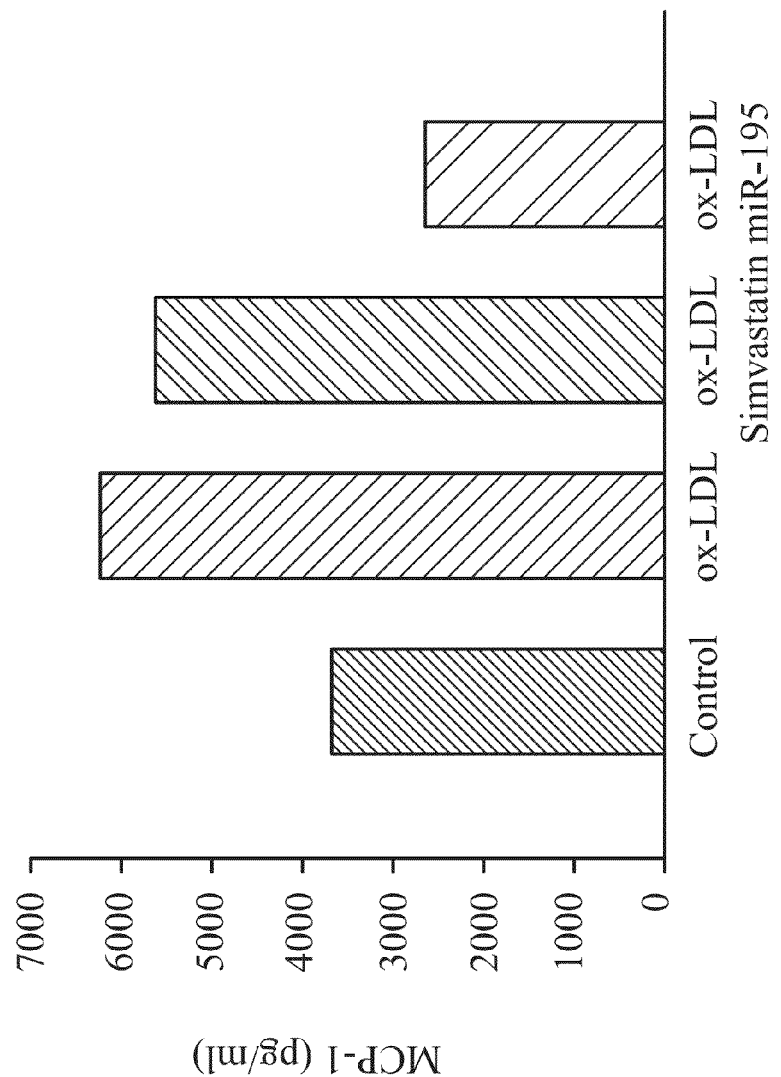
FIG. 4 shows the expression levels of an atherosclerotic biomarker, MCP-1, secreted from the VSMC cells treated with simvastatin or microRNA-195 in the presence of ox-LDL stimulation.

As shown in FIG. 4, microRNA-195 can significantly decrease MCP-1 levels. MicroRNA-195 has a stronger effect on reducing the atherogenic biomarker than simvastatin.

According to all of results in the Part 3, microRNA-195 has a strong anti-atherosclerosis effect and ability for treating atherosclerosis.

Part 4: the Serum Level of miRNA-195 in Human Subjects

The serum levels of microRNA-195 from the general population and patients who received coronary angiography were measured. Approximately 6 ml venous blood was collected from an antecubital fossa and placed in a serum separator tube. The blood was centrifuged at 1600 rpm for 5 min and then serum obtained therefrom was aliquoted into 1.7 ml Eppendorf tubes, followed by 15 minutes of high speed centrifugation at 12,000 rpm to completely remove cell debris, leaving only circulating RNA. Total RNA which included miRNA in 400 µl of serum was isolated by using a MasterPure™ complete RNA purification kit according to the manufacturer protocol (Epicentre). The RNA was stored at a temperature of −80° C. until use. The endogenous abundance of microRNAs was determined in an ABI PRIZM 7500 sequence detection system using the quantitative real-time PCR method. Each sample was performed in triplicates. The typical amplification program was carried out in a 20 µl reaction with a primer at a final concentration of 300 nM and probes of 200 nM. Serial dilutions of the control cDNA for generating standard curves ran in duplicate. Real-time PCR results were analyzed using the ABI PRISM 7500 SDS software. Relative differences of microRNAs were quantified using the ΔΔCt method. For graphical presentation, the $2^{-\Delta\Delta Ct}$ transformation was used according to the ABI user bulletin version #2. Expression values were depicted relatively to the value at baseline which was the earliest time point present in all the experiments. The results are shown in FIG. 5.

Figure 5:
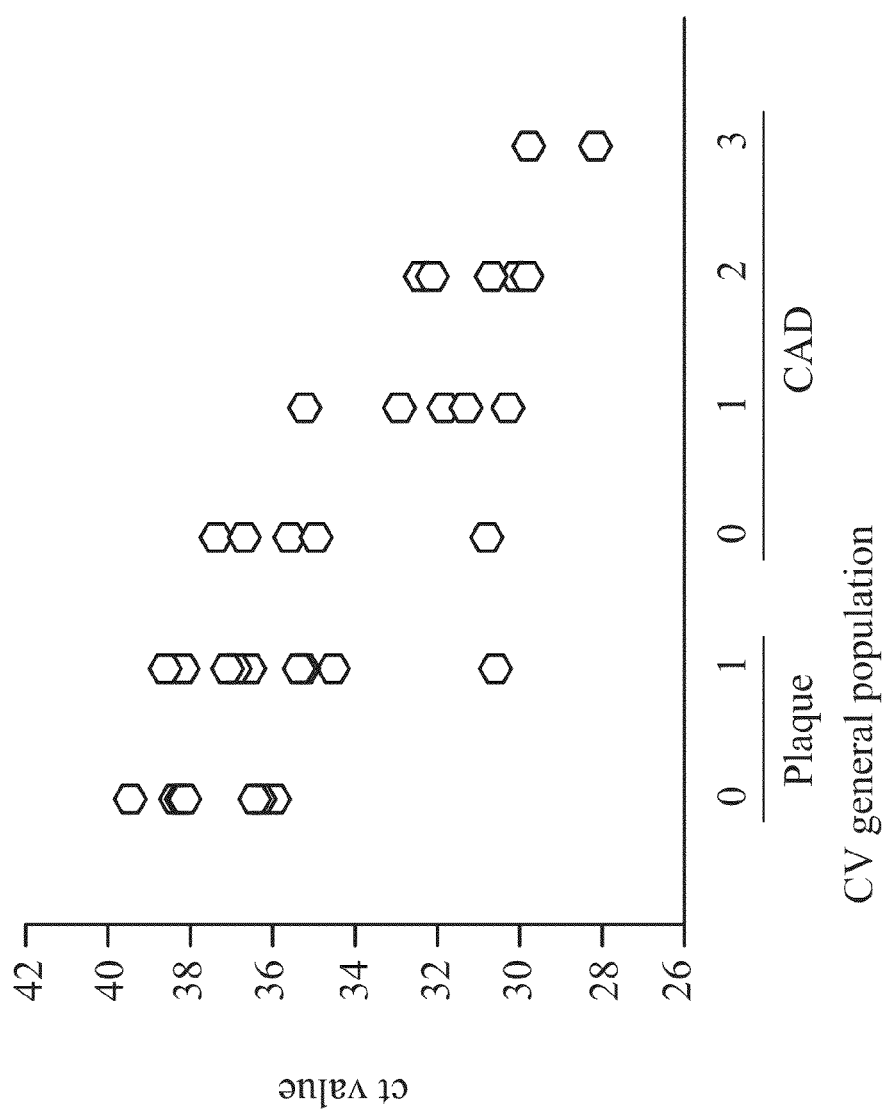
FIG. 5 shows the expression levels of microRNA-195 in the general population (the subjects were further divided into plaque=0 or 1) and the patients with coronary artery stenosis (the subjects were further divided into CAD=0, 1, 2, and 3), respectively.

As shown in FIG. 5, microRNA-195 has a great potential for the clinical application because it can be detected from peripheral blood. When microRNA-195 serum levels (i.e. endogenous microRNA-195) among the general population were compared with those from the patients who received coronary angiography, it was found that the serum microRNA-195 levels have a clear pattern with the severity of atherosclerosis. Notably, the higher Ct value shown in FIG. 5, the lower microRNA-195 concentration. We separated the general population according to their severity of atherosclerosis measured in the carotid artery: plaque=0 means no evidence of atherosclerosis and plaque=1 means detectable carotid atherosclerosis but without clinical symptoms. The patients receiving coronary angiography can be divided into 4 severity categories: CAD=0 means the stenosis of coronary artery is less than 50% in any of the three major coronary arteries, CAD=1 means the stenosis is greater than 50% in one of the three major coronary arteries, CAD=2 means the stenosis is greater than 50% in two of the three major coronary arteries and CAD=3 means the stenosis is greater than 50% in all three major coronary arteries). Clearly, the subjects with more severe atherosclerosis had higher microRNA-195 levels. To summarize: the endogenous microRNA-195 expression level of subjects with atherosclerosis is higher than that of healthy subjects which may result from a nature defense mechanism. That is, microRNA-195 is an endogenous protective factor for atherosclerosis and thus microRNA-195 will increase when a subject develops atherosclerosis. Moreover, according to the results in the Part 4, microRNA-195 may be used as an atherosclerotic biomarker for determining if a subject has atherosclerosis.

Part 5: The miRNA-195 Expression Level in the Blood Vessel of Human Subjects

Tissue Samples from

Paraformaldehyde-fixed paraffin-embedded (FFPE) arterial blood vessel samples from human subjects with or without atherosclerosis were acquired. The paraffin blocks were cut into 10-µm sections. Total RNA from the FFPE tissues block was isolated using the commercially available kits, RecoverAll Total Nucleic Acid Isolation Kit (Ambion), according to the manufacturers' instructions. Paraffin-embedded samples are incubated in xylene at elevated temperatures to solubilize and remove paraffin from the tissue, then washed in alcohol solutions to remove the xylene. After deparaffinization, it was mixed with 400 µl of digestion buffer and 4 µl of protease and was incubated at 50° C. for three hours for RNA isolation. The prepared specimen was added to 480 µl isolation additive and vortex, and then passed through a filter cartridge and incubated for five minutes. Washing was performed three times and the results were centrifuged to remove residual fluid. DNase mix was added to each filter cartridge and they were incubate for 30 minutes before elution with nucleic acid with 20 µl DEPC-distilled water and incubation for five minutes and storage at −80° C. Concentration and purity of the total RNA samples were measured using the NanoPhotometer™ spectrophotometer (IMPLEN GmbH, Munich, Germany).

Reverse Transcription and Quantitative Real-Time PCR

The RNA was stored at −80° C. until use. The endogenous abundance of microRNAs was performed in an ABI PRIZM 7500 sequence detection system. Quantitative real-time PCR was performed in triplicates. The typical amplification program is carried out in a 20 µl reaction with primer at a final concentration of 300 nM and probes of 200 nM. Serial dilutions of the control cDNA for generating standard curves will run in duplicate. Real-time PCR results can be analyzed using the ABI PRISM 7500 SDS software. Relative differences of microRNAs were quantified using the ΔΔCt method. For graphical presentation, we will use the $2^{-\Delta\Delta Ct}$ transformation according to the ABI user bulletin version #2. Expression values depict relatively to the value at baseline which is the earliest time point present in all the experiments.

The result showed that Ct value was 35.6 for the normal tissue and 34.9 for the atherosclerotic tissue. A lower Ct value which means a higher microRNA-195 in the atherosclerotic blood vessels is comparable with what observed in the serum samples as shown in FIG. 5.

Part 6: Confirmation of Endogenous microRNA of Cells with Different Treatments

The endogenous abundance of microRNAs that showed differential expressions between experimental (simvastatin, Panax Notoginseng, ox-LDL plus simvastatin or Panax Notoginseng) and control (ox-LDL) cells were measured. Quantitative real-time PCR was performed in an ABI PRIZM 7500 sequence detection system in triplicates. The typical amplification program was carried out in a 20 µl reaction with a primer at a final concentration of 300 nM and probes of 200 nM. Serial dilutions of the control cDNA for generating standard curves ran in duplicate. Real-time PCR results were analyzed using ABI PRISM 7500 SDS software. Relative differences of microRNAs were quantified using the ΔΔCt method. For graphical presentation, the $2^{-\Delta\Delta Ct}$ transformation was used according to the ABI user bulletin version #2. Expression values were depicted relatively to the value at baseline which was the earliest time point present in all the experiments. The results are shown in FIG. 6.

Figure 6:
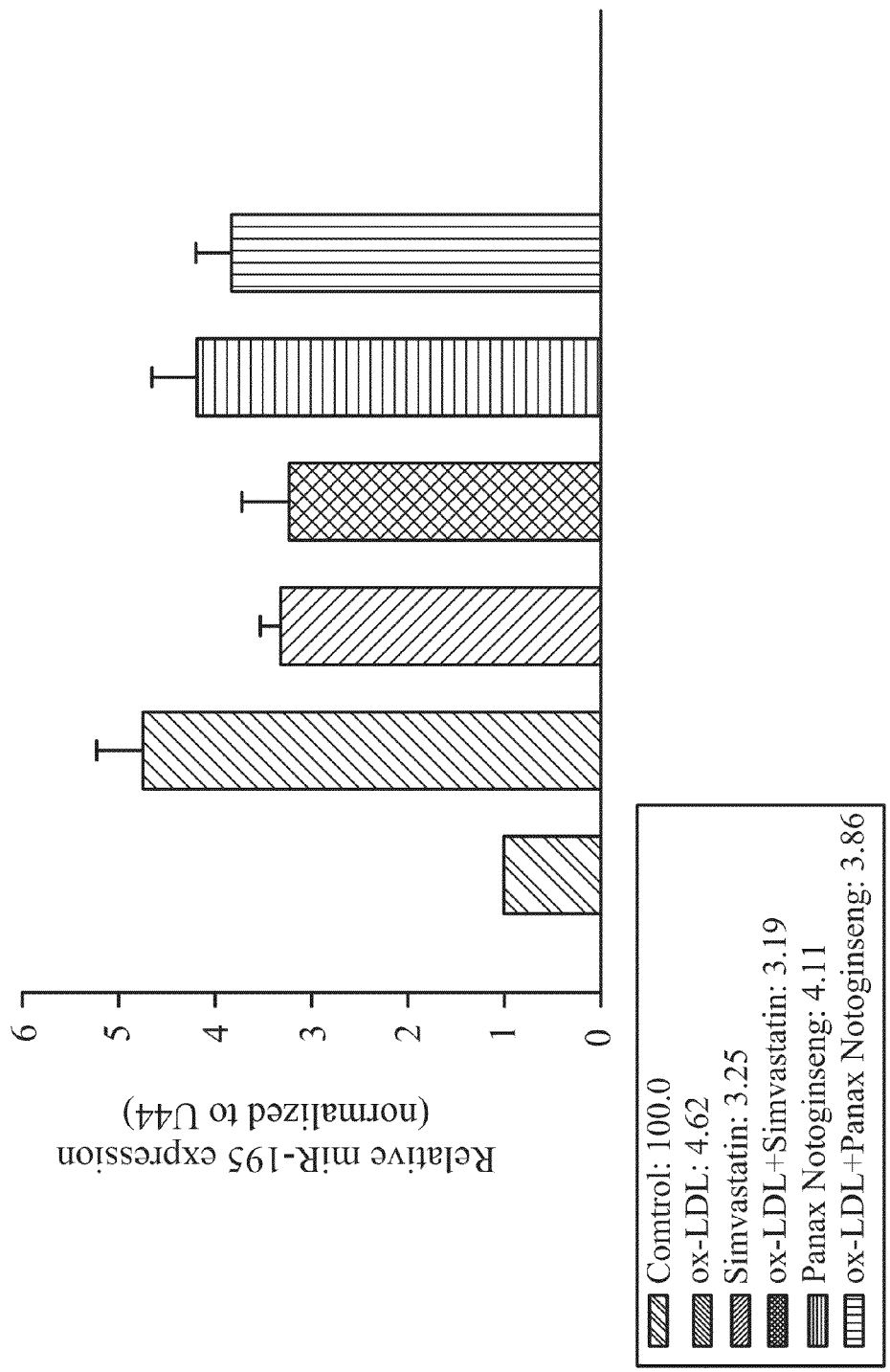
FIG. 6 shows the expression levels of microRNA-195 of the VSMC cells treated with simvastatin or Panax Notoginseng in the presence and absence of ox-LDL stimulation. The microRNA-195 abundance was normalized to U44.

As shown in FIG. 6, in order to verify the accuracy of the microarray results in the ox-LDL-stimulated VSMC, the change of endogenous microRNA-195 in the VSMC was measured after being normalized to U44. The results indicated that microRNA-195 expression of the untreated cells was increased by 4.3-fold after treatment with ox-LDL for 24 hours. After the treatment with ox-LDL and simvastatin (1 nM) or Panax Notoginseng (1 mg/ml) for 24 hours, the endogenous microRNA-195 decreased by more than a 0.68-fold and 0.84-fold than in the ox-LDL-stimulated cells. Moreover, according to the results in the Part 5, microRNA-195 can be a potential drug target for screening an anti-atherosclerotic drug since the expression of microRNA-195 decreased by simvastatin and Panax Notoginseng which are known medicine for treating atherosclerosis.

Part 7: Effect of microRNA 195 Treatment on Mice with Atherosclerotic

Construction of Lentivirus Expressing microRNA-195 and Control Lentivirus Expressing GFP Lentivector Expression System was purchased from System Biosciences. The microRNA expression vectors pCDH-CMV-MCS-EF1-GreenPuro vector (System Biosciences, SBI) contain a CMV-driven EGFP reporter. The full length sequence of microRNA-195 was amplified from genomic DNA by polymerase chain reaction (PCR). Primer pairs for microRNA expression vectors were microRNA-195 forward: 5'-CTAAAATCTCCAGGGCAGTTT-3' (SEQ ID NO: 3), and reverse: 5'-CTCTCAGCTTCGTGCTGTCTG-3' (SEQ ID NO: 4). The PCR products were inserted to the microRNA expression vectors. The clones carrying microRNA-195 was named pCDH-miR-195. The pCDH vector was used as control.

Lentivirus Production

The miRNA expression vectors (pCDH-miR-195 and pCDH mock vector) and Lentivirus Package plasmid mix (System Biosciences, SBI) were cotransfected into 293TN cells with PureFection™ Transfection Reagent (System Biosciences; Mountain View, Calif., USA), and Lenti-X Concentrator (Clontech, USA) was used for concentration. Infectious titers were determined by counting GFP positive-293T cells using a fluorescence microscope. Virus titers were at the range of $10^8$ IFU/ml medium. The pCDH mock vector were also packaged and used as a negative control which had no significant homology to mice gene sequences.

To first test whether the pCDH-miR-195 can really overexpress the microRNA-195, the pCDH-miR-195 was used to infect the human aorta smooth muscle cells. Then, microRNA-195 level from pCDH-miR-195 were measured by RT-qPCR and then compared with that from the control vector.

Treatment of apoE−/− Mice

Since apoE knockout (apoE−/−) mice are able to develop atherosclerotic plaques in the aorta in 12 weeks under a high-fat diet, this animal model can be used to examine whether microRNA-195 has the ability to prevent arterial atherosclerosis.

Figure 7:
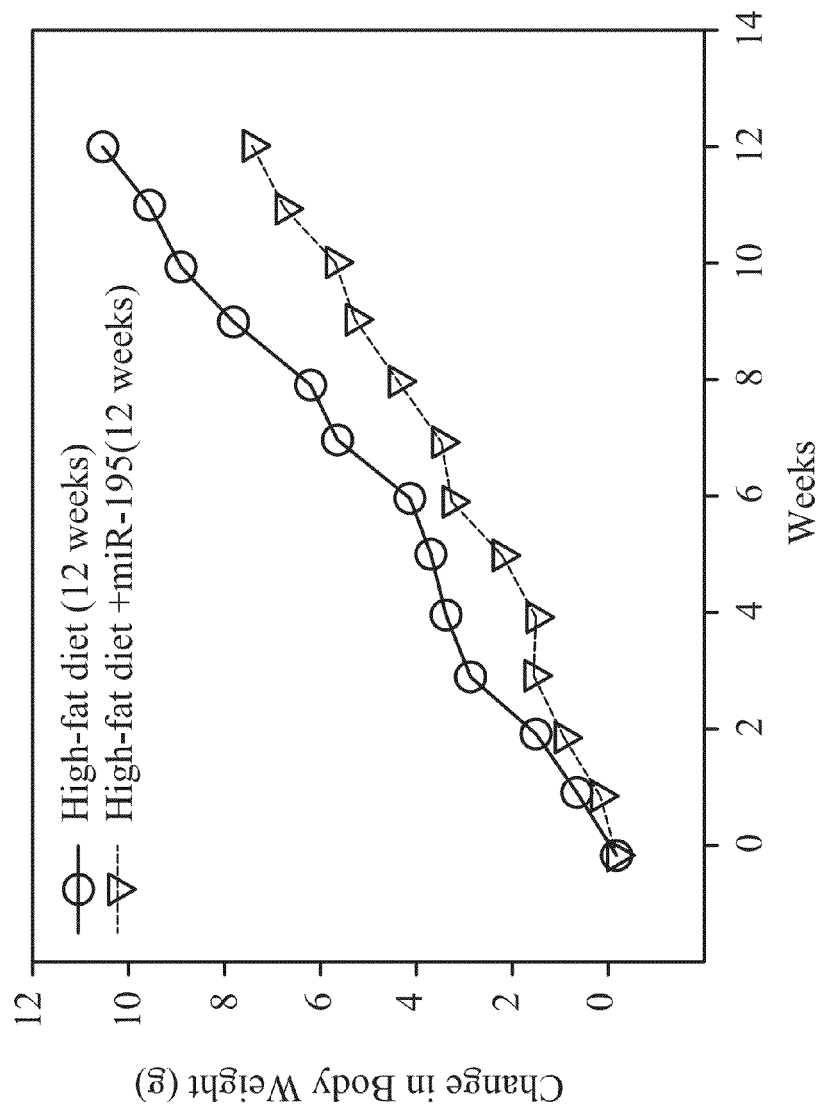
FIG. 7 shows changes in body weight of the apoE knockout (apoE−/−) mice treated with Lentivirus containing pCDH-miR-195 (the microRNA-195 treatment group) and the apoE−/− mice treated with Lentivirus containing control vector.

0.1 ml PBS with $10^7$ IFU Lentivirus containing pCDH-miR-195 or a control vector was injected to the tail veil of the apoE−/− mice that were under a high fat diet. The injection was repeated once a week for a total of 12 weeks. Changes in body weight of the apoE−/− mice treated with Lentivirus containing pCDH-miR-195 (the microRNA-195 treatment group) and the apoE−/− mice treated with Lentivirus containing the control vector (the control group) were recorded every week and are shown in FIG. 7. When the experiment was completed, the mice of the microRNA-195 treatment group and the mice of the control group were sacrificed.

Figure 8:
FIG. 8 shows the atherosclerotic plaque in the aorta of mice of the microRNA-195 treatment group and that of mice of the control group.

Biochemical indexes, such as blood urea nitrogen (BUN) and creatinine (CRE) for renal function, GOT (AST) and GPT (ALT) for liver function, fasting blood sugar (GLU), total cholesterol (T-CHO), high density lipoprotein (HDL), low density lipoprotein (LDL) and triglyceride (TG) of the blood of mice of the microRNA-195 treatment group and mice of the control group were determined and are shown in Table 2, respectively. Indexes for weight of various organs to body weight (organ weight/body weight) of mice of the microRNA-195 treatment group and the mice of the control group were determined and are shown in Table 3, respectively. Furthermore, the atherosclerotic plaque in the aorta of mice of the microRNA-195 treatment group and that of mice of the control group were determined by Oil Red stain, and the results are shown in FIG. 8.

TABLE 2

Biochemical indexes for the mice of the microRNA-195 treatment group and the mice of the control group

| Average | BUN | CRE | GOT | GPT | GLU | T-CHO | HDL | TG |
|---|---|---|---|---|---|---|---|---|
| Control | 21.5 | 0.7 | 108 | 33 | 182 | 765.5 | 6.5 | 191 |
| MicroRNA-195 | 21.5 | 0.7 | 118.5 | 28.5 | 166.5 | 711.5 | 11.5 | 141 |

TABLE 3

Indexes for weight of various organs to body weight (organ weight/body weight) of mice of the microRNA-195 treatment group and the mice of the control group

| Average (%) | Heart | Liver | Spleen | Lung | Kidney |
|---|---|---|---|---|---|
| Control | 0.51 | 3.55 | 0.33 | 0.75 | 1.19 |
| MicroRNA-195 | 0.49 | 3.35 | 0.32 | 0.72 | 1.20 |

According to FIG. 7, it is known that microRNA-195 can control the increase of body weight better than the placebo when the mice are under a high-fat diet. Furthermore, blood sugar level was lower in the microRNA-195 treated animal than the placebo treated animals. In addition, the microRNA-195 treatment also improved lipid profile better than statin in the apoE−/− mice (HDL: showed an increase of 77% by microRNA-195 as compared to 20% by statin; and for triglyceride: showed a decrease of 26% by microRNA-195 as compared to no decrease by statin) (see Table 2 and Song et al. Lipids in Health and Disease, 10:8, 2011).

In FIG. 8, the atherosclerotic plaques are red spots (indicated by the arrows) scattered in the aorta. The left aorta was from the apoE−/− mice treated with the control vector that did not carry the microRNA-195 gene (the mice of the control group). The right aorta was from the pCDH-miR-195 apoE−/− mice. The atherosclerotic plaques were reduced by 84% in the microRNA-195 treated mice, when compared to the placebo test mice (i.e. the control group). Currently, statin is the most commonly used drug to treat hyperlipidemia and atherosclerosis. However, statin can only reduce approximately 50% of atherosclerosis plaque in apoE−/− mice (Song et al. Lipids in Health and Disease, 10:8, 2011), which is less effective than microRNA-195.

Part 8: Rat Model of Balloon Injured Carotid Artery and MicroRNA-195 Transfection.

The animal experimental protocols were approved by the Animal Care and Use Committee of the Kaohsiung Medical University. The balloon-injured carotid artery was produced in male Sprague-Dawley (SD) rats (300 to 350 g). Rats were sedated with isoflurane (Abbott) anesthetized by intraperitoneal administration of ketamine hydrochloride (72 mg/kg; Sigma-Aldrich) and xylazine hydrochloride (4 mg/kg; Sigma-Aldrich). The external carotid artery (ECA) and the right internal carotid artery were exposed through a neck incision under a microscope (Carl Zeiss, Oberkochen, Germany). A 2F Fogarty catheter (Baxter Edwards) was advanced to the proximal edge of the omohyoid muscle. The balloon on the catheter was inflated with saline and then withdrew three times.

Figure 9:
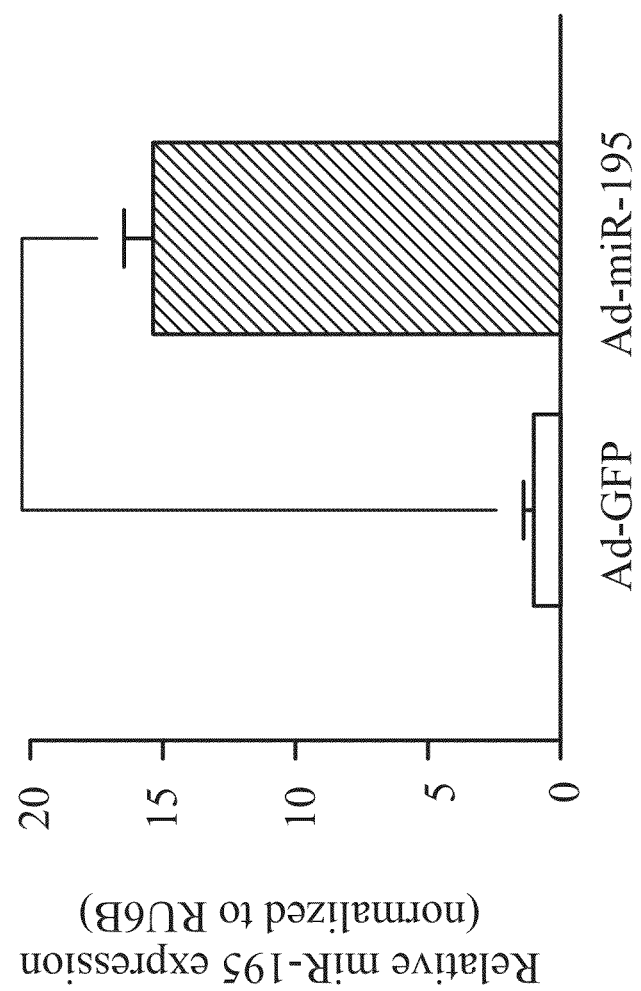
FIG. 9 shows microRNA-195 expression of cells transfected with Ad-miR-195 and that of cells transfected with Ad-GFP.
Figure 10:
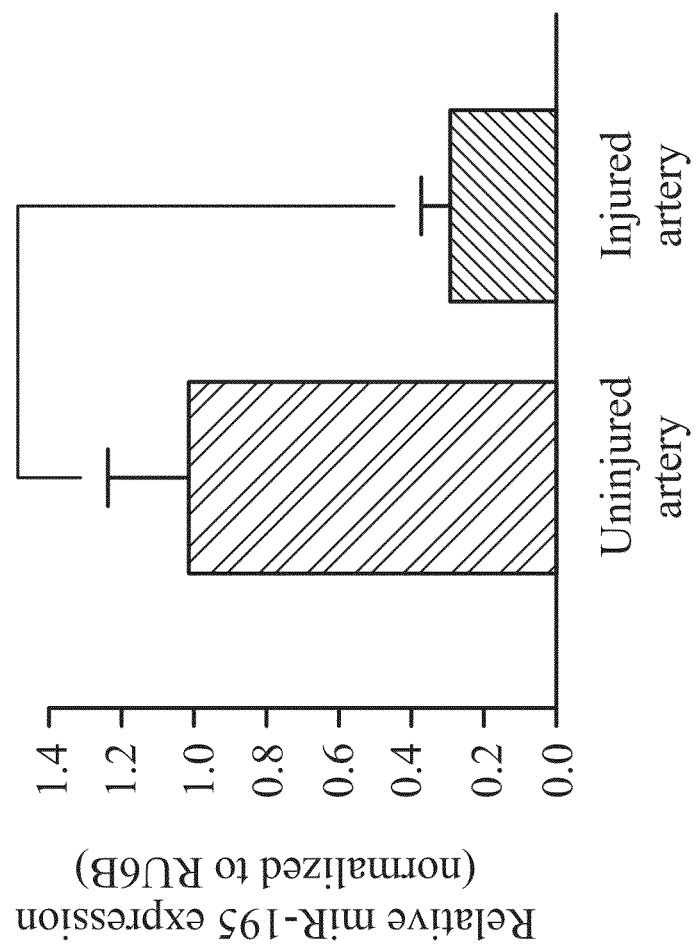
FIG. 10 shows microRNA-195 expression of the injured arteries and that of the uninjured arteries.
Figure 11:
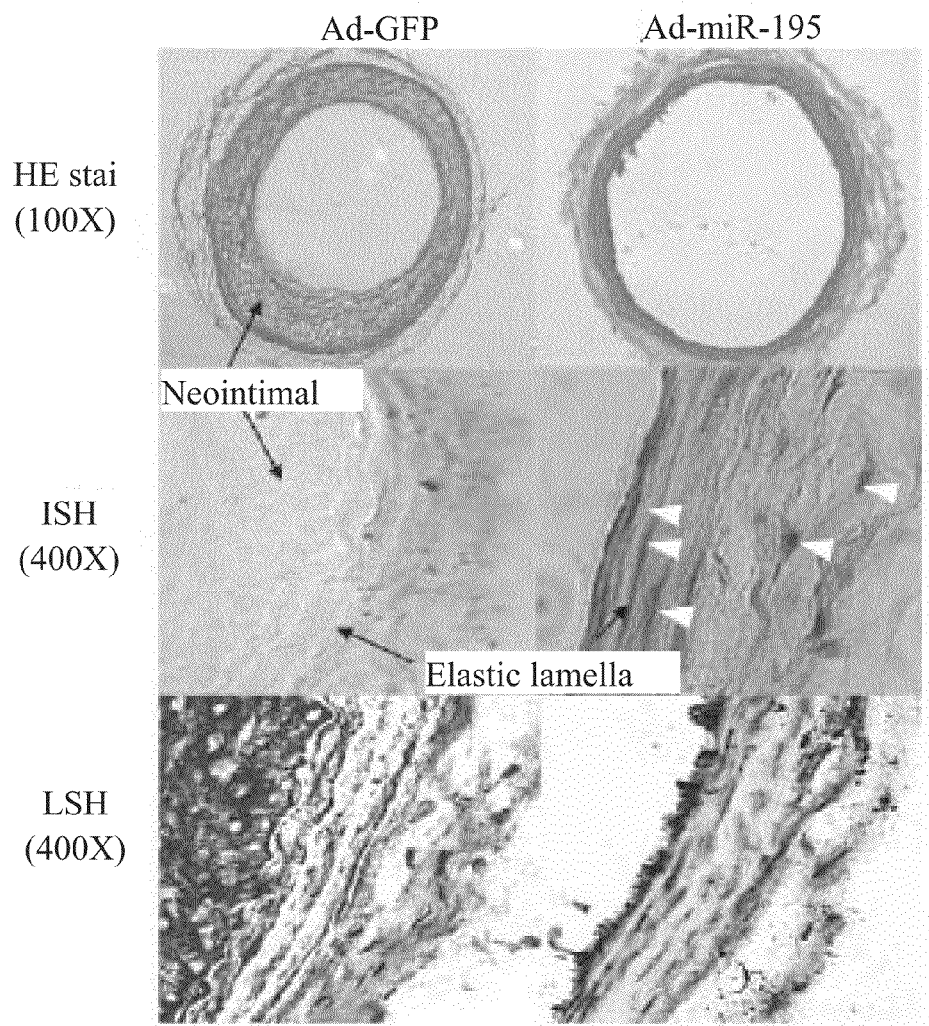
FIG. 11 shows results of eosin stain, situ hybridization, and immunohistochemistry for Ad-miR-195-treated arteries and Ad-GFP-treated arteries, respectively.

A microRNA-195 gene therapy was conducted in a rat model. The delivery efficacy of adenovirus expressing microRNA-195 (Ad-miR-195) or adenovirus expressing green fluorescent protein (Ad-GFP) to HASMCs was first confirmed. A 15-fold increase of microR-195 expression was seen in the cells transfected with Ad-miR-195, as compared with those transfected with Ad-GFP (FIG. 9; P=0.0009), which indicated Ad-miR-195 can successfully synthesize microRNA-195. After the balloon injury in the carotid artery, the solution of (50 μl) adenovirus expressing microRNA-195 (Ad-miR-195) ($5×10^7$ pfu/ml) or adenovirus expressing green fluorescent protein (Ad-GFP) was infused into the ligated segment of the common carotid artery (CCA) for 30 min (n=5 in the Ad-GFP group; n=5 in the Ad-miR-195 group). A histological examination with 12-μm sections of carotid rings with hematoxylin and eosin stain was performed four weeks after surgery. Subsequently, the expression of endogenous microRNA-195 in the wall of the carotid artery of the rats after balloon injury was measured. The level of endogenous microRNA-195 was significantly lower in the injured arteries than in the uninjured arteries by 80% (FIG. 10; P=0.0069). When Ad-miR-195 was administered to the balloon injured carotid artery, neointimal formation was significantly reduced (FIG. 11 upper panel). To confirm that the inhibitory effect of exogenous microRNA-195 on neointimal formation was mediated through restoring the downregulated microRNA-195, in situ hybridization (ISH) (W. Nakajima et al., J Neurosci 20, 7994, 2000) was performed on the carotid artery section. The ISH data indicated that microRNA-195 was present in the smooth muscle cells of the intimal layer and in the fibroblasts of the medial layer in the Ad-miR-195-treated arteries (FIG. 11 middle panel). In contrast, no microRNA-195 was detected in the Ad-GFP-treated arteries. The experiment of immunohistochemistry (IHC) for Cdc42 protein showed that this protein was more abundant in the neointima of the Ad-GFP treated arteries than in the Ad-miR-195 treated arteries (FIG. 11 bottom panel). The Cdc42 protein was primarily found in the endothelial cells and smooth muscle cells of neointima. These results suggested that increased Cdc42 protein expression in the balloon-injured artery led to neointimal growth, and microRNA-195 suppressed the expression of Cdc42 resulting in the inhibition of neointimal formation.

Part 9: Effect of MicroRNA-195 on Endothelial Cells

Endothelial dysfunction is considered an early marker for atherosclerosis, preceding angiographic or ultrasonic evidence of atherosclerotic plaque. The integral role of the endothelial cells in vascular health and of endothelial dysfunction in atherosclerosis has been a major issue in vascular biology. Accordingly, the effect of microRNA-195 no endothelial function was investigated as follows.

Smooth muscle cell (SMC)'s microRNA-195 can improve endothelial function by reducing monocyte adhesion An increase of SMC's microRNA-195 by transfection improves endothelial function: a reduction of adhesion of monocytes (THP-1 cells).

MicroRNA Transfection

MicroRNA-195 mimic, microRNA-195 inhibitor and negative control microRNA (NC-miR) were purchased from Ambion Inc. (TX, USA) with the sequences information shown as microRNA-195 mimic, 5'-UAGCAGCACA-GAAAUAUUGGC-3' (SEQ ID NO: 5); microRNA-195 inhibitor, 5'-GCCAATATTTCTGTGCTGCTA-3' (SEQ ID NO: 6); negative control sequence, 5'-AGUACUGCUUAC-GAUACGG-3' (SEQ ID NO: 7). MicroRNA-195 inhibitor was used to specifically bind to and inhibit endogenous microRNA-195. The NC-miR is a random sequence pre-miR molecule that has been extensively tested in human cell lines and tissues and validated to produce no identifiable effects on known miRNA function. By using Lipofectamine 2000 reagent, miR-195 mimic and Pre-miR Negative Control were transfected into SMC for 24 hours.

Co-Culture System

At first, human aorta smooth muscle cells (HASMCs) were seeded on the inner side of Millicell® with the PET membrane (Millipore, Hanging 24-well cell culture inserts) at a density of $3×10^5$ cells/cm² and transfected with microRNA-195 mimic mimic by using lipofectamine 2000 for 24 hours. In the meanwhile, endothelial cells were seeded onto the tissue culture well at a density of $4×10^5$ cells/cm². Human umbilical venous endothelial cells (HUVEC) and HASMCs were maintained in their respective medium to grow to confluence. After following 24 hours pre-incubation, microRNA-195-treated HASMCs on the inner surface of PET membranes were co-incubated with HUVEC culture in DMEM/10% FBS. The HUVEC-HASMC co-culture was rinsed 3 times with 1 ml of phosphate-buffered saline (PBS, pH 7.3) to wash out the culture medium. Then 4 ml of new culture medium was put in each dish and they were incubated overnight at 37° C. in 5% $CO_2$ and 95% air humidified atmosphere to get ready for use in adhesion experiments of THP-1 cells.

In Vitro Adhesion Assay

To visualize the THP-1 cells adherent to the HUVEC-HASMC co-culture, the THP-1 cells were labeled with a fluorescent dye, calcein-AM. Fluorescence-labeled cells were resuspended in 4 ml of IMDM containing 10% FCS and prepared for use in adhesion experiments. Then 20-30 μl of suspension of calcein-AM-labeled THP-1 cells containing 1.0×104 cells was added to the HUVEC-HASMC co-culture dish and they were incubated for 4 hours at 37° C. in 5% $CO_2$ and 95% air humidified atmosphere. After that, the suspension of THP-1 cells in each dish was discarded, and the monoculture and co-culture were gently washed three times with 1 ml of PBS at pH 7.3 in order to remove non-adherent THP-1 cells. The number of adherent THP-1 cells was determined by measuring the fluorescence intensity of the adherent THP-1 cells using a Fluoroskan Asent® FL (Thermo Labsystem, Helsinki, Finland) and also by counting the number of adherent fluorescence-labeled THP-1 cells that were seen under a fluorescence microscope (Nikon, Japan) which encompassed a surface area of 0.314 mm². Measurements were carried out at 6 different areas and the results were expressed as the number of THP-1 cells per mm².

Western Blot 30 mg of the cytoplasmic protein extracts were boiled in sample buffer (125 mM Tris-HCl, pH 6.8 1% v/w SDS, 10% v/v glycerol, 0.1% bromophenol blue, 2% v/v 2-mercaptoethanol) for 5 minutes. Samples were separated by 12% SDS-PAGE and transferred to a Hybond-ECL membrane (Amersham, Buckinghamshire, UK). Membranes were probed with rabbit antiserum to human eNOs, VCAM-1, ICAM-1, VE-cadherin and Sirt1 diluted 1:500 in TBS. The protein-antibody complexes were detected by using an HRP-conjugated secondary antibody by the super-signal enhanced chemiluminescence system (Pierce). The expression of α-tubulin were detected by anti-α-tubulin antibody (Sigma), for a quantity control.

Figure 12:
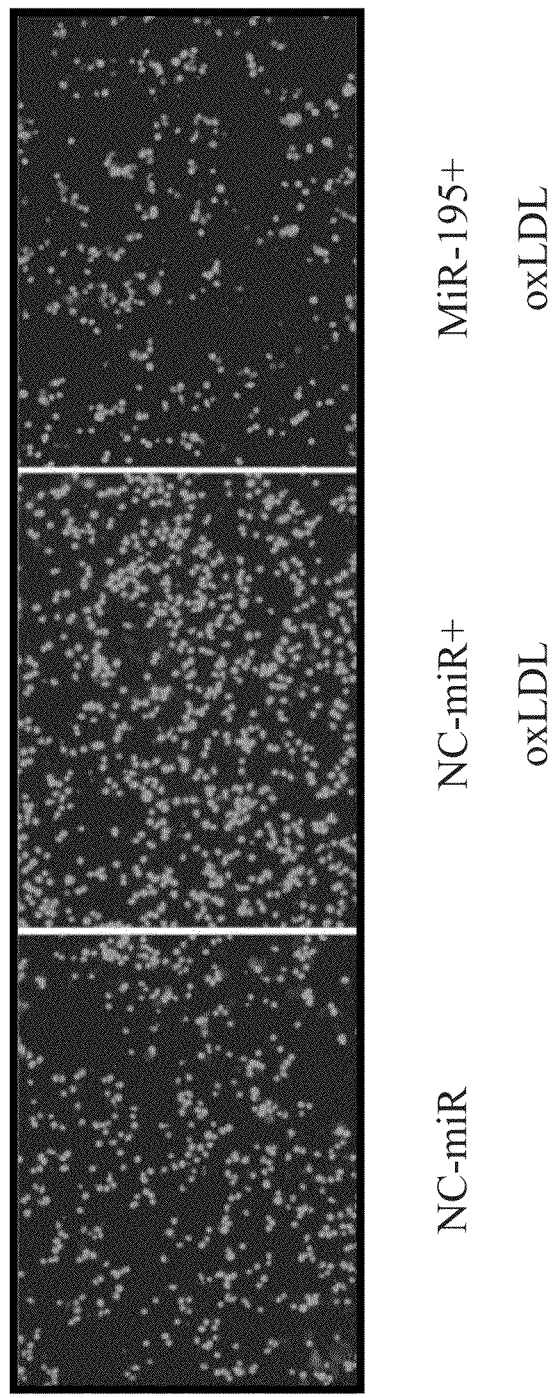
FIG. 12 shows monocyte adhesion for HUVEC co-cultured with SMCs transfected with negative control microRNA, HUVEC co-cultured with SMCs transfected with negative control microRNA in the presence of ox-LDL and HUVEC co-cultured with SMCs transfected with microRNA-195 in the presence of ox-LDL, respectively.
Figure 13:
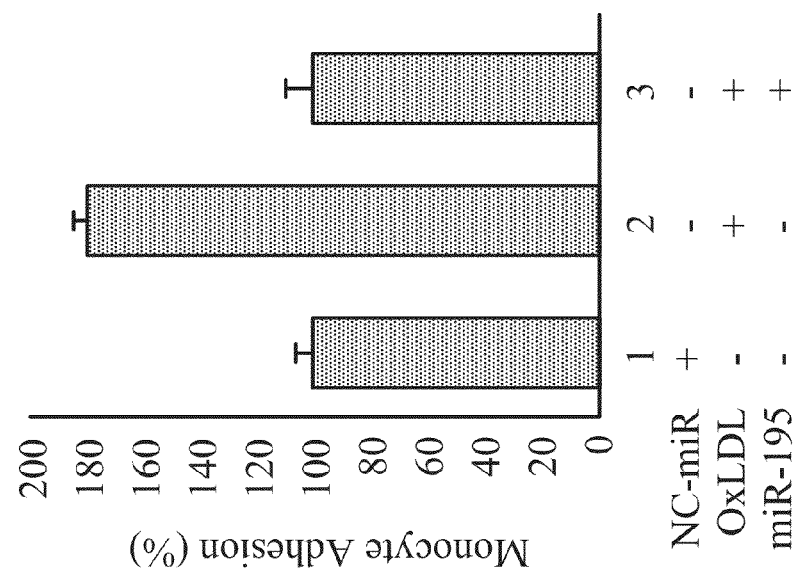
FIG. 13 shows the quantification data for FIG. 12.

FIG. 12 shows that THP-1 cells (a human monocytic cell line) adhere to HUVEC while they are co-cultured with HASMCs transfected with negative control microRNA (NC-miR) (on the left of FIG. 12). FIG. 12 shows that more THP-1 cells adhere to HUVEC in the presence of ox-LDL while they are co-cultured with HASMCs transfected with negative control microRNA (NC-miR) (in the middle of FIG. 12). FIG. 12 further shows that fewer THP-1 cells adhere to HUVEC in the presence of ox-LDL while they are co-cultured with HASMCs transfected with microRNA-195 (on the right of FIG. 12). FIG. 13 shows the quantification data for FIG. 12.

Figure 14:
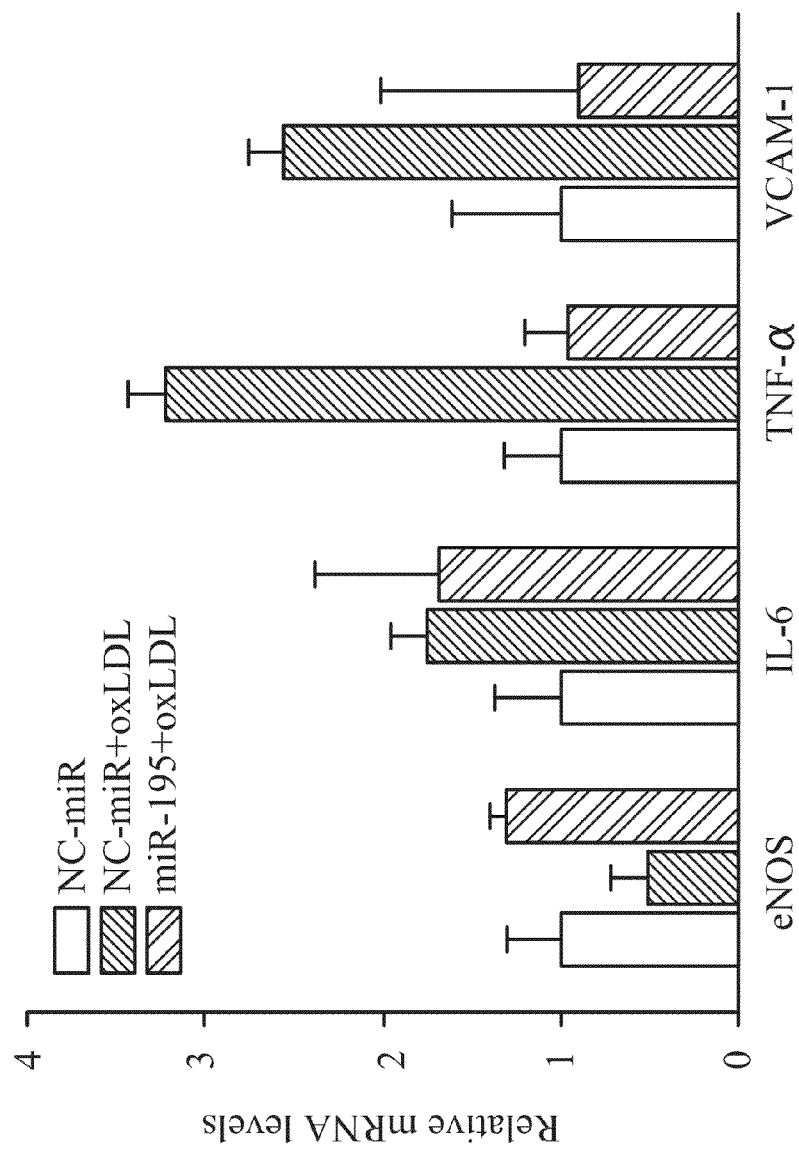
FIG. 14 shows mRNA levels for VCAM-1, TNF-α, IL-6, and eNOS in HUVECs co-cultured with microRNA-195 transfected SMCs.

HASMC's microRNA-195 can improve several biomarkers surrogating endothelial functions HASMCs were transfected with negative control microRNA or microRNA-195 with or without the presence of oxLDL. MicroRNA-195-transfected HASMCs were co-cultured with HUVEC. Real-time qPCR analysis of mRNA levels for genes surrogating endothelial functions as well as atherosclerosis, such as vascular cell adhesion molecule-1 (VCAM-1), tissue necrosis factor-α (TNF-α) and interleukin-6 (IL-6), and vasodilation gene, endothelial nitric oxide synthase (eNOS), were determined in HUVECs. The results are shown in FIG. 14. The results show that HASMC's microRNA-195 suppresses atherosclerotic genes (IL-6, TNF-α and VCAM-1) and increases the vasodilation gene (eNOS) in HUVECs While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for treating atherosclerosis in a subject in need thereof, comprising administering an effective amount of microRNA-195 to the subject in need thereof to inhibit or decrease atherosclerosis in the subject.

2. The method for treating atherosclerosis in a subject in need thereof as claimed in claim 1, wherein the microRNA-195 is packaged in a pharmaceutically acceptable carrier.

3. The method for treating atherosclerosis in a subject in need thereof as claimed in claim 2, wherein the pharmaceutically acceptable carrier comprises a liposome, lipid particle or viral vector.

4. The method for treating atherosclerosis in a subject in need thereof as claimed in claim 1, wherein the subject comprises a mammal.

5. The method for treating atherosclerosis in a subject in need thereof as claimed in claim 4, wherein the mammal comprises a human.

6. The method for treating atherosclerosis in a subject in need thereof as claimed in claim 1 further comprising administering an effective amount of statin to the subject to inhibit or decrease atherosclerosis in the subject.

7. The method for treating atherosclerosis in a subject in need thereof as claimed in claim 6, wherein the statin comprises simvastatin.

8. The method for treating atherosclerosis in a subject in need thereof as claimed in claim 6, wherein the microRNA-195 and the statin are administered at the same time.

9. The method for treating atherosclerosis in a subject in need thereof as claimed in claim 1 further comprising administering an effective amount of water extract of Panax Notoginseng to the subject to inhibit or decrease atherosclerosis in the subject.

10. The method for treating atherosclerosis in a subject in need thereof as claimed in claim 9, wherein the microRNA-195 and the water extract of Panax Notoginseng are administered at the same time.

11. The method for treating atherosclerosis in a subject in need thereof as claimed in claim 1 further comprising administering an effective amount of saponin to the subject to inhibit or decrease atherosclerosis in the subject.

12. The method for treating atherosclerosis in a subject in need thereof as claimed in claim 11, wherein the microRNA-195 and the saponin are administered at the same time.

* * * * *

```
                        SEQUENCE LISTING

<160> NUMBER OF SEQ ID NOS: 7

<210> SEQ ID NO 1
<211> LENGTH: 21
<212> TYPE: RNA
<213> ORGANISM: Homo sapiens

<400> SEQUENCE: 1
uagcagcaca gaaauauugg c                                             21

<210> SEQ ID NO 2
<211> LENGTH: 87
<212> TYPE: RNA
<213> ORGANISM: Homo sapiens

<400> SEQUENCE: 2
agcuucccug gcucuagcag cacagaaaua uuggcacagg gaagcgaguc ugccaauauu   60
ggcugugcug cuccaggcag gguggug                                       87

<210> SEQ ID NO 3
<211> LENGTH: 21
<212> TYPE: DNA
<213> ORGANISM: Artificial sequence
<220> FEATURE:
<223> OTHER INFORMATION: microRNA-195 forward primer

<400> SEQUENCE: 3
ctaaaatctc cagggcagtt t                                             21

<210> SEQ ID NO 4
<211> LENGTH: 21
<212> TYPE: DNA
<213> ORGANISM: Artificial sequence
<220> FEATURE:
<223> OTHER INFORMATION: microRNA-195 reverse primer

<400> SEQUENCE: 4
ctctcagctt cgtgctgtct g                                             21
```

-continued

```
<210> SEQ ID NO 5
<211> LENGTH: 21
<212> TYPE: RNA
<213> ORGANISM: Artificial sequence
<220> FEATURE:
<223> OTHER INFORMATION: microRNA-195 mimic

<400> SEQUENCE: 5
uagcagcaca gaaauauugg c                                             21

<210> SEQ ID NO 6
<211> LENGTH: 21
<212> TYPE: DNA
<213> ORGANISM: Artificial sequence
<220> FEATURE:
<223> OTHER INFORMATION: microRNA-195 inhibitor

<400> SEQUENCE: 6
gccaatattt ctgtgctgct a                                             21

<210> SEQ ID NO 7
<211> LENGTH: 19
<212> TYPE: RNA
<213> ORGANISM: Artificial sequence
<220> FEATURE:
<223> OTHER INFORMATION: negative control microRNA

<400> SEQUENCE: 7
aguacugcuu acgauacgg                                                19
```